(12) United States Patent
Collinge et al.

(10) Patent No.: US 7,435,423 B2
(45) Date of Patent: Oct. 14, 2008

(54) WOUND TREATMENT MEDIUM AND METHOD OF PACKAGING AND USE

(76) Inventors: Cory Collinge, 1325 Pennsylvania Ave., Suite 890, Fort Worth, TX (US) 76104; Kevin Kelly, 5109 Alaire Dr., Fort Worth, TX (US) 76132

( * ) Notice: Subject to any disclaimer, the term of this patent is extended or adjusted under 35 U.S.C. 154(b) by 229 days.

(21) Appl. No.: 11/243,843

(22) Filed: Oct. 5, 2005

(65) Prior Publication Data

US 2007/0077280 A1 Apr. 5, 2007

(51) Int. Cl.
*A61F 13/00* (2006.01)
(52) U.S. Cl. .................... 424/400; 424/443; 424/444; 424/445; 424/446; 424/447
(58) Field of Classification Search .............. 424/400, 424/443, 444, 445, 446, 447, 449
See application file for complete search history.

(56) References Cited

U.S. PATENT DOCUMENTS

| 4,401,651 | A | 8/1983 | Knutson | 424/80 |
| 5,201,704 | A | 4/1993 | Ray | 604/49 |
| 5,281,419 | A | 1/1994 | Tuan et al. | 424/426 |
| 5,756,127 | A | 5/1998 | Grisoni et al. | 424/489 |
| 6,040,493 | A | 3/2000 | Cooke et al. | 602/41 |
| 6,648,133 | B1 | 11/2003 | Blaschke et al. | 206/221 |

*Primary Examiner*—Ruth A Davis
(74) *Attorney, Agent, or Firm*—Charles D. Gunter, Jr.

(57) ABSTRACT

A sterile wound treatment kit includes a plastic container pouch with a sealed outer periphery which forms a sterile interior region which isolates the pouch interior from a surrounding environment. A drug absorbing medium is located within the pouch interior and initially isolated from the surrounding environment by the sealed periphery. A syringe accepting fitting is located on the pouch for discharging a treatment drug from a syringe into the pouch interior. The pouch interior is large enough to allow the drug absorbing medium to be shaken within the pouch interior once a drug is injected into the sterile interior region, whereby the drug absorbing medium will contact and evenly absorb the drug treatment. The pouch can be opened at the time of use to allow access to the drug absorbing medium so that the medium can be applied to a wound site.

11 Claims, 3 Drawing Sheets

WOUND TREATMENT MEDIUM AND METHOD OF PACKAGING AND USE

BACKGROUND OF THE INVENTION

1. Field of the Invention

The invention relates to a device and method for helping to prevent infection and for aiding tissue repair in the treatment of an injured mammal that involves the medical treatment and healing process of injured soft tissue and damaged osseous material such as is found in the case of a compound fracture wound.

2. Description of the Prior Art

Wound management is a significant portion of nearly all modern medical practice environments. Wounds occur from a large variety of sources including, to name a few, burns, blunt trauma, chronic ulceration, skin lacerations, tissue abscesses and irritation, open bone fractures (compound fracture), and pressure sores. Such wounds and their treatment constitute a large percentage of the treatment provided to medical patients. The best treatment for these wounds is complete a cleansing and sterile treatment, as close to the time and site of injury as possible.

Compound or "open" fractures are a relatively common occurrence in society today. In a compound fracture the bone undergoes sufficient trauma that it literally breaks into pieces and tears through the skin. Once the bone is in communication with the outer environment, the wound and fracture site is then highly susceptible to infection. In order to properly heal, the bone must be placed back into alignment and held in place for a sufficient length of time for the piece of bone to be fused together by way of new bone growth. The bone must be properly aligned or "reduced" for the bone to heal properly. In order to hold the two pieces of bone in the correct position, surgical intervention is usually necessary, typically involving the placement of a suitable retention device. The retention device can be a plate or apparatus which is attached by screws or some similar mechanism on the outside of the bone. In the alternative, a retention pin or rod which is disposed in the cavity extending through the center of the bone is used in some cases.

Osteomyelitis is a bone infection caused by destructive microorganisms, most commonly, *staphylococcus aureus*. Very often, infection reaches the bone via compound fracture. It is known that a large number of open fractures are contaminated with various types of bacterial organisms prior to any surgical intervention. The growth of microorganisms in an open fracture environment is enhanced by the impaired vascularity, debris deposited in the wound, and loss of skeletal stability. Some of the worst and most difficult to treat infections are "hospital-acquired" or "nosocomial" infections, where virulent hospital flora may cause the infection. This has clearly been seen for cases of traumatic wounds and compound fractures where the wounds have been left without aseptic wound coverage in the hospital and have become infected. Infection may seriously complicate the healing process and may lead to extended hospital stays, loss of limb, and in some cases, even death. Infections are generally recognized as being a primary cause of non-union and bony instability following open fractures. Thus, a chief objective in the treatment of open fractures is not only to stabilize osseous structures, but also to prevent soft tissue and bony infections.

There is often an 8-24 hour window for surgical treatment of wounds such as the compound fractures described above. This may be due to the lack of immediate availability of a surgeon, to the lack of availability of needed hospital facilities, and for a variety of other causes. As a result, it is often necessary to treat wounds of the above type with some sort of wound cleansing and debridement technique as a temporary treatment measure until surgery can be performed.

A large number of methods for wound cleansing and debridement have been developed in the past. Those methods include wound cleansers such as povidone-iodine, hydrogen-peroxide, acetic acid, and chlorinated solutions, which however, have a toxic effect on cells. Other types of wound cleaning and debridement include the use of broad spectrum antibiotics, piston type syringe irrigation, wet to dry saline gauze dressings, surgical/mechanical debridement, enzymatic debridement, antibiotic impregnated beads, and pulsed lavage. The utilization of antibiotic therapy has been shown to be extremely important, and perhaps the most important, intervention in reducing the incidence of infection in the case of compound fracture wounds. A device or medium that can deliver a high local dose of antibiotic is thus desirable. The prognosis of patients undergoing antimicrobial therapy is determined by the bactericidal level of antibiotics delivered at the locale of the infected site.

A persistent problem with treating any localized infection by systemic administration of antibiotics is that the relationship between the assayed serum antibiotic concentration and the level present at the site of the infection is inconsistent, especially when the local site is traumatized tissue. Antibiotic concentrations are often subtherapeutic due to impaired vascularity at the fracture site, devitalized bony fragments, and/or associated systemic complications. Consequently, high doses of parenteral antibiotics must often be used to achieve adequate local concentrations. The high doses are not only costly, but more importantly increase the incidence of systemic side effects. The treatment of infection due to compound fracture, or other cause, has been known to fail due to the inability to achieve adequate antibiotic levels at the infected local.

Traumatic soft tissue wounds are also a setting in which antibiotics must be employed in a timely manner. Frequent admissions to the Emergency Department are the result of blunt or penetrating trauma and rarely gun shot wounds. Complicating the care of these patients, these wound are often contaminated by skin and environmental bacteria. Direct administration of antibiotics to the wound may help reduce the risk of local and systemic infections.

Chronic soft tissue wounds such as decubitus ulcers, diabetic wounds, and others present a great challenge to the treatment teams. These areas of devitalized tissue require frequent dressing changes and the use of wound cleansers that can have toxic effects on the healing tissues. Further complicating the management of these patient's wounds are the precipitating cause of the infection. Patients who suffer from decubitus ulcers are often bed bound which can falsely decrease serum creatinine concentrations which are used as a marker of renal function. Inaccurate serum creatinine levels due to decreased muscle mass and lack of mobility mask serious renal dysfunction. Systemic antibiotic dosing can be difficult without an accurate assessment of renal function and may lead to overdosing of antibiotics that can have serious toxic side effects.

There exists, therefore, an unmet need for an antibiotic treatment medium and method that are appropriate for use with acute and chronic soft tissue wounds.

Such systems should be able to localize the concentration of antibiotic to the area of injury, for example, the bone and surrounding local traumatized tissues of an open fracture, or at the site of a chronic wound such as a decubitus ulcer, while avoiding problems associated with administering high doses of antibiotic systemically.

There also exists a need for such a medium and delivery system which incorporates simple and inexpensive sterile packaging, which is simple in design and which could utilize variations of existing commercially available components of medical supplies of the type traditionally used in wound treatment. Such medium and delivery systems could be utilized by the military in the field of battle as well as during man made and natural disasters where the infrastructure is not sufficient to support parenteral antibiotic administration.

SUMMARY OF THE INVENTION

Shown herein are a novel wound treatment kit and method of use which are appropriate for use in applying a wound treatment medium onto an injured portion of a mammalian body, the treatment medium being impregnated with a treatment drug, whereby the drug is released from the medium to contact and penetrate the wound area. The wound area may particularly relate to compromised bone, for example, the type found in compound fracture wounds.

The wound treatment kit of the invention includes a container pouch formed of flexible plastic, the container pouch having an exterior, an interior and a sealed outer periphery, the sealed outer periphery forming a sterile interior region which isolates the pouch interior from a surrounding environment. A drug absorbing medium is located within the pouch interior and initially isolated from the surrounding environment by the sealed periphery. A syringe accepting fitting, such as a Leur Lock or other fitting, is located on the pouch for discharging a drug treatment from a syringe into the pouch interior. The pouch interior is selectively sized relative to the drug absorbing medium to allow the medium to be shaken or manipulated within the pouch interior once a drug is injected into the sterile interior region, whereby the drug absorbing medium will contact and evenly absorb the treatment drug. In the preferred embodiment of the invention, the drug absorbing medium is a piece of sterile gauze pad. The preferred treatment drugs are broad spectrum antibiotics.

The container pouch can conveniently be formed of two overlaying sheets of flexible plastic, the sheets of flexible plastic having an adhesive applied around an outer periphery thereof to form a sealed pouch. The Leur Lock or other fitting has a syringe receiving end and an opposite end. The opposite end can be engaged between the two overlaying sheets of flexible plastic at a point on the periphery thereof, the opposite end also extending at least part way into the pouch interior region for dispensing a treatment drug into the interior region. Preferably, the container pouch can be peeled one sheet from the other in a "peel pack" form or the flexible plastic used to form the container pouch has a thickness which is selected to allow the pouch to be opened by tearing by hand.

In the method of the invention, a wound such as a compound fracture wound or other as described, is treated by providing a sterile gauze pad within the sterile interior region of a container pouch as previously described. The pouch can be sold in bulk to medical treatment facilities. At the facility, the appropriate medical personnel decide which treatment drug is appropriate for the wound in question and the drug is then injected into the container pouch by dispensing the drug from a syringe through the Leur Lock or other fitting on the pouch. The drug is evenly dispersed through the sterile gauze pad by merely shaking or massaging the container pouch for several seconds. The container pouch is then opened, either by peeling the plastic apart from one another, tearing by hand, or by cutting the pouch with scissors, thereby allowing access to the sterile gauze pad. The pad can then be removed and applied to the site of the wound. Because the container pouch containing the sterile gauze pad is supplied in bulk to a medical facility and because the treatment drug is only injected into the pouch interior region shortly before application to the wound of a patient, a large quantity of wound treatment kits can be stored for an indefinite period of time until they are needed. Any of a number of different drugs of choice may be selected by a physician for injection into the pouch interior for ultimate application to the wound.

Additional objects, features and advantages will be apparent in the written description which follows.

DETAILED DESCRIPTION OF THE INVENTION

Figure 1:
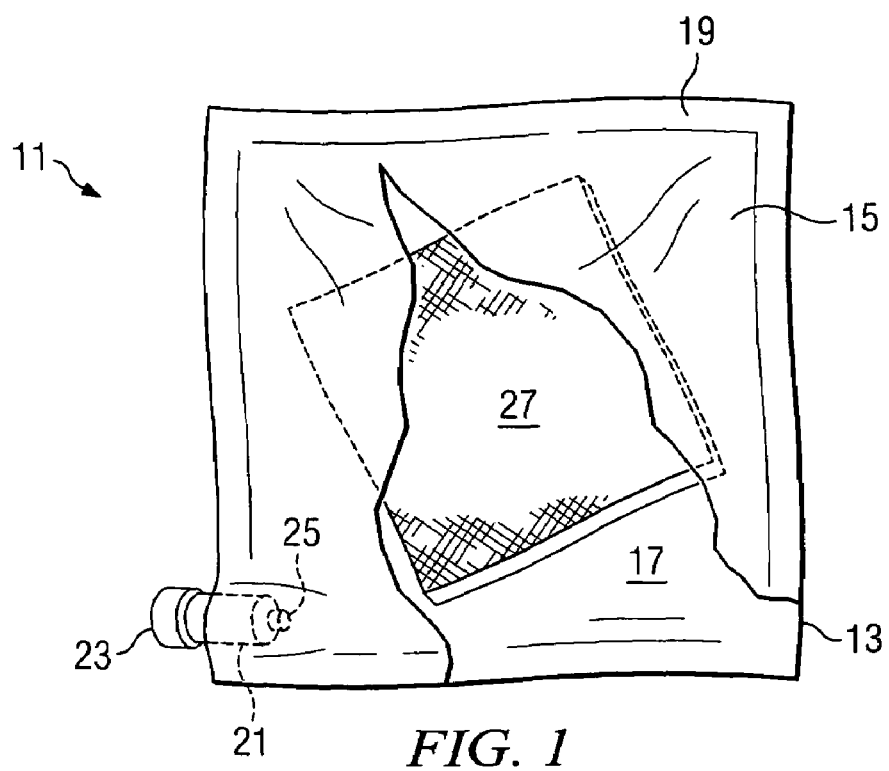
FIG. 1 is a perspective view, partly broken away, of the wound treatment kit of the invention prior to impregnating the treatment medium with a treatment drug.

Turning to FIG. 1, there is shown a sterile wound treatment kit of the invention designated generally as 11. The kit 11 comprises a container pouch formed of a flexible material, such as a suitable plastic. The container pouch 13 has an exterior 15, an interior 17 and a sealed outer periphery 19. The sealed outer periphery 19 forms a sterile interior region 17 which isolates the pouch interior from a surrounding environment. The flexible plastic chosen for the container pouch can be any convenient commercially available material such as the commonly known polyolefins such as polypropylene, polyethylene, etc.

Preferably, the container pouch 13 is formed of two overlaying sheets of flexible plastic. The sheets of flexible plastic having an adhesive applied around the outer periphery 19 thereof to form the sealed pouch. Alternative sealing techniques can also be utilized, such as by forming the sealed peripheral region by heat treating and thereby sealing the peripheral edges of the pouch.

A syringe accepting fitting, such as the Leur-Lock or other fitting 21 is located on the pouch for discharging a treatment drug from a syringe into the pouch interior 17. The syringe accepting fitting 21 has as syringe receiving end 23 and an opposite end 25. The opposite end 25 can be engaged between the two overlaying sheets of flexible plastic at a point on the periphery thereof. The opposite end 25 extends at least part way into the pouch interior 17, or otherwise communicates with the pouch interior, for dispensing a treatment drug into the interior region 17.

The flexible plastic material which is selected for the container pouch 13 preferably has a thickness and strength properties which allow the pouch to be opened by simply tearing the pouch by hand. Alternatively, a thicker or stronger material may be utilized and the pouch may be opened by cutting with scissors or otherwise puncturing the pouch.

A drug absorbing medium 27 is located within the pouch interior 17 and initially isolated from the surrounding environment by the sealed periphery 19. The preferred drug absorbing medium is a piece of sterile gauze pad, although other porous carrier mediums may be employed as well. The dimensions of the pouch interior 17 are selectively sized relative to the size of the drug absorbing medium 27 to allow the medium to be shaken within the pouch interior 17 once a drug is injected to the sterile interior region through the syringe accepting fitting 21. In this way, the drug absorbing medium 27 will contact and evenly absorb the treatment drug. The particular treatment drug selected will vary depending upon the nature and extent of the wound and other factors. Preferably, the treatment drug is a broad spectrum antibiotic. Known antibiotics of this general type include, e.g., Cephazolin, Tobramycin and Gentamycin. Other antibiotic drugs may also be used, including those having specialized purposes, such as those antibiotics which are effective under anaerobic conditions.

Figure 3:
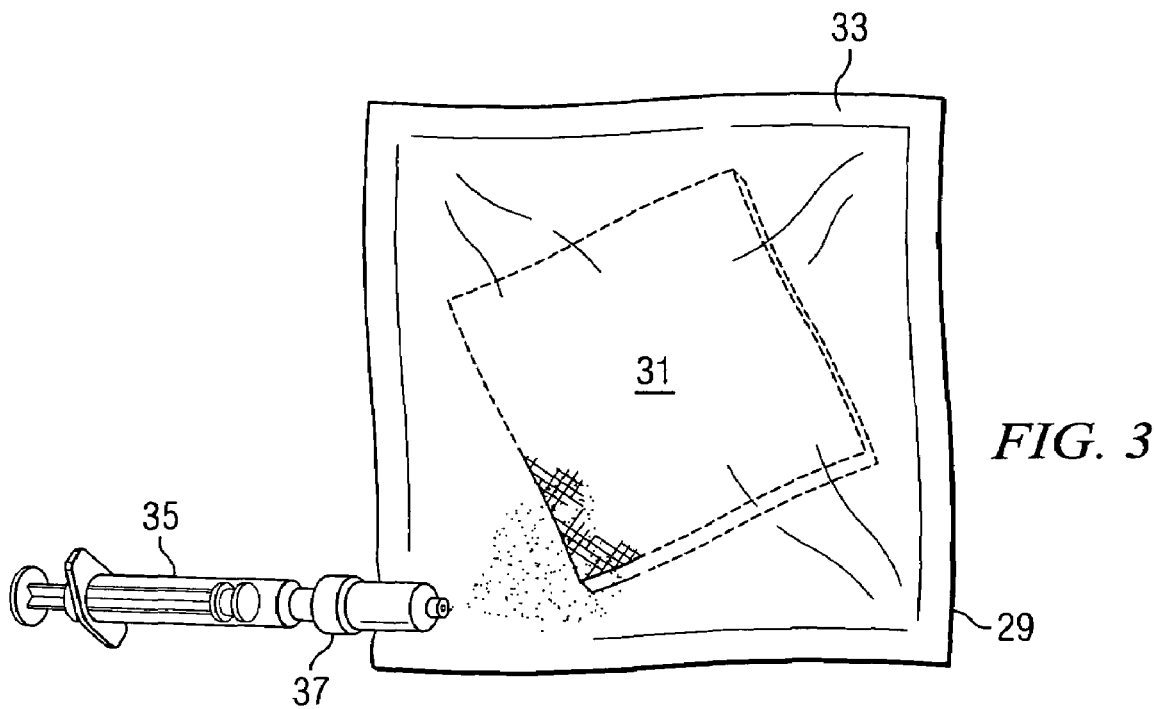
FIGS. 3-5 are simplified illustrations of the steps of the method of the invention in utilizing the wound treatment kit of the invention in treating a wound.
Figure 4:
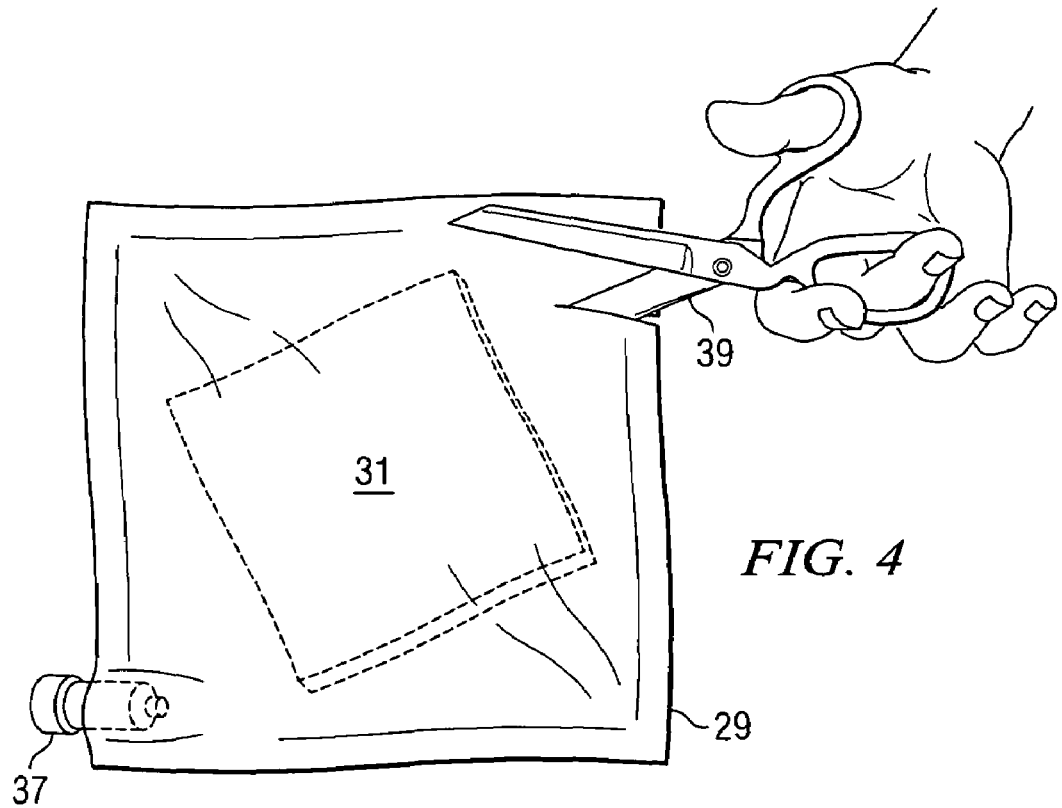
Figure 5:
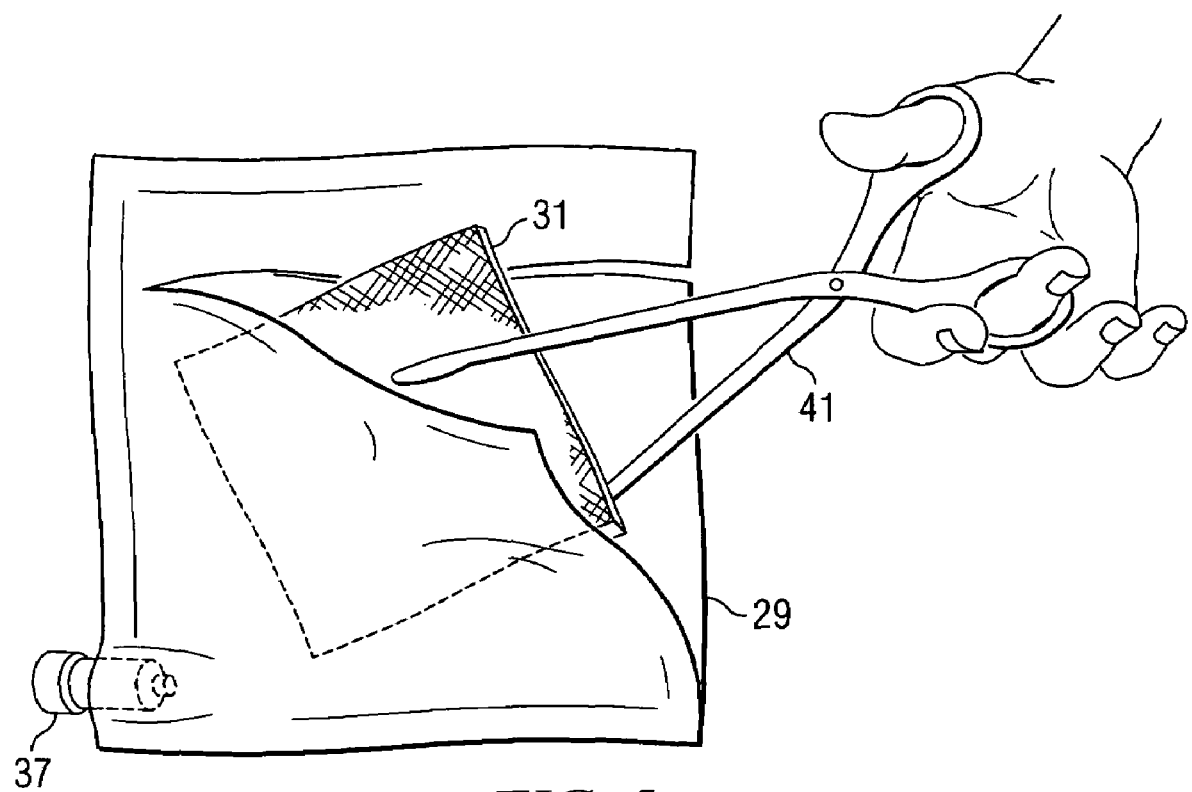

The method of treating a wound by applying a sterile treatment medium will now be explained with reference primarily to FIGS. 3-5. A container pouch 29 (FIG. 3) is provided formed of a flexible plastic, as previously described. The sterile drug absorbing medium, in this case a sterile gauze pad 31, is placed within the pouch interior with the sealed outer periphery 31 forming a sterile interior region which isolates the pouch interior from the surrounding environment.

A treatment drug of choice is then discharged into the pouch interior by installing the needle of the syringe 35 within the barrel of the syringe accepting fitting 37 and discharging the drug from the syringe into the pouch interior. The pouch is then agitated in some fashion, as by shaking by hand, in order to evenly impregnate the gauze pad 31 with the treatment drug.

Typically, the sealed pouch 29 is supplied in bulk to the medical facility and has an extended shelf storage life. The treatment drug would not be typically discharged through the syringe accepting fitting 37 until shortly before the time of expected use. This would insure that the treatment drug was relatively fresh and effective.

After the treatment medium has had sufficient time to absorb the treatment drug, the container pouch 29 would be opened in some fashion and the sterile gauze pad 31 applied to the wound site. In one embodiment of the invention, the plastic material of the container pouch 29 is peeled one side away from the other to maintain maximal sterility. A sufficiently thin or weak is also envisioned to allow the pouch to be opened by simply tearing by hand. In some cases, it may be necessary to puncture the pouch in some other fashion, as shown by cutting with scissors 39 in FIG. 4. FIG. 5 shows the sterile gauze pad 31 which is now impregnated with the treatment drug being grasped with a sterile instrument 41 which is used to apply the gauze pad to the wound site.

Figure 2:
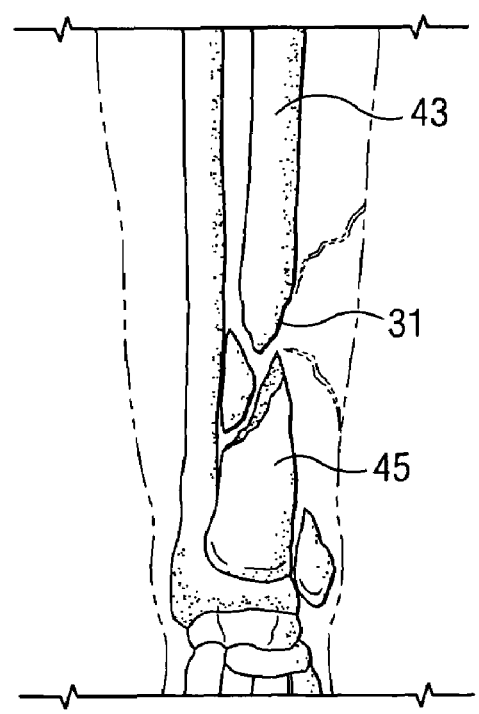
FIG. 2 is a simplified view of a compound fracture wound of the type which might be treated with the device and method of the invention.

FIG. 2 is a simplified view of a compound fracture wound of the leg in which one of the large bones is actually split into two separate pieces 43, 45. A gauze pad 31 has been placed over the bone ends 43, 45 at the wound site and the wound has been temporarily covered. This technique might be used to temporarily stabilize a wound overnight until the necessary surgery to fix the severed bones and address the soft tissues could be accomplished, for example, the next morning. These techniques could also be employed, as described above, in the treatment of penetrating wounds, as well as chronic wounds that are the result of diabetes, venous stasis ulcers, decubitus and other soft tissue ulcerations.

An invention has been provided with several advantages. The sterile wound treatment kit of the invention is simple in design and economical to manufacture. The wound treatment kit can be assembled by making minor modifications to several commercially available treatment materials. The kits are shelf stable for an extended period of time and are only "activated" when a treatment drug of choice is injected through the syringe accepting fitting into the pouch interior. Applying a physical treatment medium, such as sterile gauze pad, has been found to be more effective than parenteral treatment methods in some cases providing a higher concentration of antibiotic locally at the wound site. For example, a typical through-the-vein antibiotic might have a volume of distribution of, at best, 1 gram per 5.6 liters of fluid. More commonly, these antibiotics penetrate into many areas of the body (e.g. brain, skin, lungs, etc.) and as a result, the concentration that is delivered to the site of injury is much less because of the antibiotics wide distribution. The reduced concentration at the injured site may not allow for antibiotic concentrations that are above the minimum inhibitory concentration require to inhibit the growth of the bacteria contaminating the wound. The above described wound treatment method would provide on the order of 1 gram per liter of inhibitory concentration of antibiotic at the wound site. Applicant's treatment method would therefore provide well above the minimum inhibitory concentration of antibiotic desired, with minimal risks of side effects. Additionally, removal of the gauze pad at the time of subsequent surgery typically removes a certain quantity of dead tissue with the gauze. This may relieve the surgeon of some of the time consuming chore of removing dead tissue from the wound site.

While the invention has been shown in only one of its forms, it is thus limited but is susceptible to various changes and modifications without departing from the spirit thereof.

What is claimed is:

1. A method of treating a wound by applying a sterile drug treatment medium, the method comprising the steps of:
    providing a container pouch formed of flexible plastic, the container pouch having an exterior, an interior and a sealed outer periphery, the sealed outer periphery forming a sterile interior region which isolates the pouch interior from a surrounding environment;
    placing a sterile drug absorbing medium within the pouch interior prior to sealing the outer periphery, whereby the sterile drug absorbing medium is initially isolated from the surrounding environment by the sealed periphery;
    providing a syringe accepting fitting on the pouch for discharging a drug treatment from a syringe into the pouch interior;
    installing a syringe within the fitting on the container pouch and discharging a selected treatment drug from the syringe into the pouch interior, the pouch interior being selectively sized relative to the drug absorbing medium to allow the medium to be shaken within the pouch interior once a drug is injected into the sterile interior region, whereby the drug absorbing medium will contact and evenly absorb the drug treatment;
    shaking the pouch to cause the treatment drug to be evenly absorbed by the medium so that the medium is impregnated with the drug;
    opening the container pouch to allow access to the drug impregnated medium; and
    applying the drug impregnated medium to a wound site.

2. The method of claim 1, wherein the drug absorbing medium which is placed within the interior region of the pouch is a piece of sterile gauze pad.

3. The method of claim 2, wherein the treatment drug is a broad spectrum antibiotic.

4. The method of claim 3, wherein the antibiotic impregnated gauze pad is used to pack the wound of a compound fracture.

5. The method of claim 1, wherein the syringe accepting fitting is a Leur Lock fitting.

6. A method of treating a compound fracture wound by applying a sterile treatment medium which has been impregnated with an antibiotic treatment drug, the method comprising the steps of:

provuding a container pouch formed of flexible plastic, the container pouch having an exterior, an interior and a sealed outer periphery, the sealed outer periphery forming a sterile interior region which isolates the pouch interior from a surrounding environment, the container pouch being formed of two overlaying sheets of flexible plastic, the sheets of flexible plastic having an adhesive applied around the outer periphery thereof to form the sealed pouch;

placing a piece of sterile gauze pad within the pouch interior prior to sealing the outer periphery, whereby the sterile gauze pad is initially isolated from the surrounding environment by the sealed periphery;

providing a Leur Lock or other syringe accepting fitting on the pouch for discharging a drug treatment from a syringe into the pouch interior;

installing a syringe within the Leur Lock fitting on the container pouch and discharging a selected antibiotic treatment drug from the syringe into the pouch interior, the pouch interior being selectively sized relative to the sterile gauze pad to allow the gauze pad to be shaken within the pouch interior once a drug is injected into the sterile interior region, whereby the gauze pad will contact and evenly absorb the antibiotic drug treatment;

shaking the pouch to cause the treatment drug to be evenly absorbed by the gauze pad so that the gauze pad is impregnated with the drug;

opening the container pouch to allow access to the drug impregnated gauze pad; and applying the gauze pad to a compound fracture or other wound site and temporarily covering the wound to thereby allow the treatment drug to contact and penetrate the wound site.

7. The method of claim 6, wherein the Leur Lock has an opposite end and wherein the opposite end is engaged between the two overlaying sheets of flexible plastic at a point on the periphery thereof, the opposite end also extending at least part way into the pouch interior region for dispensing a treatment drug into the interior region.

8. The method of claim 7, wherein the container pouch is opened by tearing the pouch by hand.

9. The method of claim 7, wherein the container pouch is opened by cutting the pouch with scissors.

10. The method of claim 6, wherein the container pouch containing the sterile gauze pad is supplied in bulk to a medical facility and wherein the treatment drug is injected into the pouch interior region shortly before application to the wound of a patient.

11. The method of claim 10, wherein any of a number of different antibiotic drugs may be selected by a physician for injection into the pouch interior for ultimate application to the wound.

* * * * *